(12) United States Patent
de Graaff et al.

(10) Patent No.: US 8,808,744 B2
(45) Date of Patent: *Aug. 19, 2014

(54) DRUG DELIVERY SYSTEM BASED ON POLYETHYLENE VINYLACETATE COPOLYMERS

(71) Applicant: Merck Sharp & Dohme B.V., Rahway, NJ (US)

(72) Inventors: Wouter de Graaff, Oss (NL); Janneke Sophie Groen, Oss (NL); Marcus Antonius Bernardus Kruft, Oss (NL); Johannes Antonius Hendrikus Van Laarhoven, Oss (NL); Herman Vromans, Oss (NL); Raymond Zeeman, Oss (NL)

(73) Assignee: Merck Sharp & Dohme B.V., Haarlem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/910,250

(22) Filed: Jun. 5, 2013

(65) Prior Publication Data

US 2013/0266632 A1    Oct. 10, 2013

Related U.S. Application Data

(63) Continuation of application No. 10/594,104, filed as application No. PCT/EP2005/051189 on Mar. 16, 2005, now Pat. No. 8,481,079.

(51) Int. Cl.
*A61K 9/14*    (2006.01)

(52) U.S. Cl.
USPC .......................................................... 424/484

(58) Field of Classification Search
None
See application file for complete search history.

(56) References Cited

U.S. PATENT DOCUMENTS

| | | | |
|---|---|---|---|
| 3,995,633 A | 12/1976 | Gougeon | |
| 3,995,634 A | 12/1976 | Drobish | |
| 4,237,885 A | 12/1980 | Wong et al. | |
| 4,292,965 A | 10/1981 | Nash et al. | |
| 4,596,576 A | 6/1986 | de Nijs | |
| 6,544,546 B1 | 4/2003 | Groenewegen et al. | |

FOREIGN PATENT DOCUMENTS

| | | |
|---|---|---|
| EP | 0 050 867 A1 | 5/1982 |
| EP | 0 876 815 A1 | 11/1998 |
| WO | 97/02015 A1 | 1/1997 |
| WO | 99/30976 A1 | 6/1999 |

OTHER PUBLICATIONS

Sam, A.P., "Controller release contraceptive devices: a status report", Journal of Controlled Release, 1992, p. 35-46, vol. 22.
Van Laarhoven, J.A.H. et al., "In vitro release properties of etonogestrel and ethinyl estradiol from a contraceptive vaginal ring", International Journal of Pharmaceutics, 2002, p. 163-173, vol. 232.
Zaneveld, L. J. et al., "Use of mandelic acid condensation polymer (SAMMA), a new antimicrobial contraceptive agent, for vaginal prophylaxis", Fertility and Sterility, 2002, p. 1107-1115, vol. 78, No. 5.

*Primary Examiner* — Paul Dickinson
(74) *Attorney, Agent, or Firm* — Janet E. Fair; Anna L. Cocuzzo

(57) ABSTRACT

A drug delivery system consisting of one or more compartments and comprising a progestogenic compound dissolved in a thermoplastic polyethylene vinylacetate copolymer whereby,
  if the delivery system consists of one compartment, the compartment comprises
(i) a core of a thermoplastic polyethylene vinylacetate copolymer comprising the progestogenic compound, such progestogenic compound being dissolved in the polyethylene vinylacetate copolymer up to a concentration below the saturation level at 25° C., and an estrogenic compound; and
(ii) a skin of a thermoplastic polyethylene vinylacetate copolymer covering the core, said skin being permeable for both compounds;
  if the delivery system consists of more than one compartment, only one compartment comprises
(iii) the progestogenic compound, such progestogenic compound being dissolved in a core of a thermoplastic polyethylene vinylacetate copolymer up to a concentration below the saturation level at 25° C., and an estrogenic compound; and
(iv) a skin of a thermoplastic polyethylene vinylacetate copolymer covering the core, said skin being permeable for both compounds.

16 Claims, 2 Drawing Sheets

Figure 1:
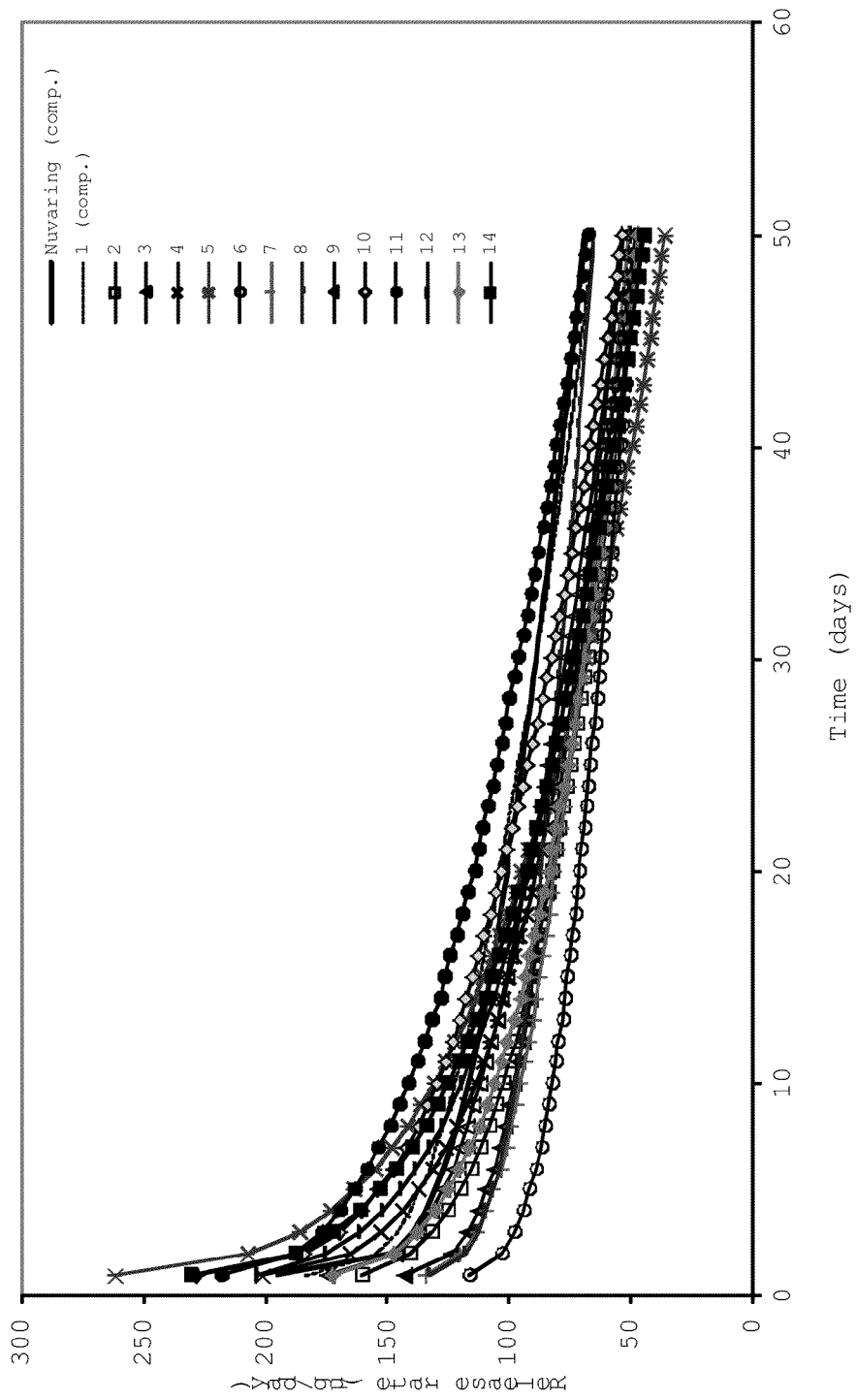

In-vitro release rates of etonogestrel for a number of drug delivery systems described in examples 2-14 according to the invention and two comparative examples.

Curve fit of the vinylacetate content of polyethylene vinylacetate copolymers summarized in table II versus the saturation level of etonogestrel in these same copolymers at 25°C and at 37°C.

DRUG DELIVERY SYSTEM BASED ON POLYETHYLENE VINYLACETATE COPOLYMERS

CROSS-REFERENCE TO RELATED APPLICATIONS

This application is a continuation of U.S. application Ser. No. 10/594,104 which is a U.S. National Phase application under 35 U.S.C. §371 of PCT Application No. PCT/EP2005/051189, filed Mar. 16, 2005, which published as WO2005/089723 A1 on Sep. 29, 2005 and claims priority under 35 U.S.C. §365(b) from European patent application No. 04101215.4, filed Mar. 24, 2004.

FIELD OF THE INVENTION

The present invention relates to the field of female contraception and hormone replacement therapy.

The invention relates to a drug delivery system, its manufacture and its use, to make a kit or a combination preparation.

BACKGROUND TECHNOLOGY

Drug delivery systems, especially those intended for intravaginal use are known in the art.

U.S. Pat. No. 3,995,633 and U.S. Pat. No. 3,995,634 describe separate, preferably spherical or cylindrical, reservoirs containing different active substances, which are assembled in specially constructed holders.

U.S. Pat. No. 4,237,885 describes a tube or coil of polymeric material which is divided into portions by means of a plurality of "spacers" provided in the tube, after which each of the separate tube portions is filled with a different active substance in a silicone fluid and the two ends of the tube are subsequently connected to one another. In this release system, however, transport (diffusion) of active material from one reservoir to the other takes place through the wall of the tube, especially upon prolonged storage, so that the pre-set fixed release ratio between the active substances in question will change over a period of time.

EP-A-0050867 discloses a two-layered vaginal ring which comprises a pharmacologically acceptable supporting ring covered by two layers preferably of silicone elastomers whereby the inner layer is a silicone elastomer loaded with an active substance.

A ring-shaped silicone vaginal delivery system has been described in U.S. Pat. No. 4,292,965. The use of silicone elastomers is nowadays considered to be less safe and is clearly no longer the material of choice.

U.S. Pat. No. 4,596,576 describes a two-compartment vaginal ring wherein each compartment contains a different active substance. To achieve a suitable ring with a constant release ratio between the various active substances, the end portions of the compartments are joined by glass stoppers.

Drug delivery systems for intravaginal use, and in particular vaginal rings, prepared of polyethylene vinylacetate (EVA) copolymers are also known in the art.

For example, J. A. H. van Laarhoven et al., International Journal of Pharmaceutics 232 (2002) pages 163-173, describes the use of EVA copolymers for the preparation of a vaginal ring.

WO-A-97/02015 describes a two-compartment device: a first compartment consisting of an EVA copolymer core, an EVA copolymer etonogestrel-loaded middle layer and an EVA copolymer non-medicated outer layer; and a second compartment consisting of an EVA copolymer core, loaded with both etonogestrel and ethinyl estradiol, and an EVA copolymer non-medicated outer layer. The preparation of the two-compartments device requires the cutting of fibres in the required lengths and the assembly of the pieces to a ring-shaped device.

EP-A-876815 describes a one-compartment vaginal ring comprising an EVA copolymer core comprising ethinyl estradiol and etonogestrel; and a non-medicated EVA copolymer skin. The progestogenic steroid etonogestrel is dissolved in the EVA copolymer core material in a concentration above the saturation level.

Among the above disclosures, EP-A-876815 clearly sets a standard; it involves a one-compartment design, it obviates the need for silastic polymer by using EVA combinations, and it releases two or more active substances in a substantially constant ratio to one another over a prolonged period in time.

Although the vaginal ring described in EP-A-876815 fulfills its purpose and provides contraception, the design can still be improved upon. The drug delivery device disclosed in EP-A-876815 is physically stable only when stored below room temperature. It requires storage and transport below room temperature, which is expensive and requires a lot of attention. As indicated in EP-A-876815 the progestogen may eventually crystallize out on the exterior surface of the vaginal ring. Such a crystallization of progestogen onto the skin of the device may lead to uncontrolled and high burst release.

It is therefore desirable to avoid the possibility of crystallization of the progestogen on the exterior surface of the vaginal ring when it is stored on or above room temperature (i.e. about 25° C.). At the same time, however, the amounts of progestogen released and release rate should remain unchanged, to ensure a sufficient pharmaceutical effect for use in contraception and/or Hormone Replacement Therapy (HRT).

An improved drug delivery device, easy to prepare, whilst avoiding the possibility of exterior crystallization of the progestogenic compound and still providing sufficient amounts and rates of release of the progestogenic compound for use in contraception and/or HRT has now been found.

SUMMARY OF THE INVENTION

Accordingly, the present invention provides a drug delivery system consisting of one or more compartments and comprising a progestogenic compound dissolved in a thermoplastic polyethylene vinylacetate copolymer whereby, if the delivery system consists of one compartment, the compartment comprises (i) a core of a thermoplastic polyethylene vinylacetate copolymer comprising the progestogenic compound, such progestogenic compound being dissolved in the polyethylene vinylacetate copolymer up to a concentration below the saturation level at 25° C., and an estrogenic compound; and (ii) a skin of a thermoplastic polyethylene vinylacetate copolymer covering the core, said skin being permeable for both compounds;

if the delivery system consists of more than one compartment, only one compartment comprises (iii) the progestogenic compound, such progestogenic compound being dissolved in a core of a thermoplastic polyethylene vinylacetate copolymer up to a concentration below the saturation level at 25° C., and an estrogenic compound; and (iv) a skin of a thermoplastic polyethylene vinylacetate copolymer covering the core, said skin being permeable for both compounds.

The improved drug delivery system is physically stable under room temperature conditions (about 25° C.) and thus does not need special storage and transportation conditions at a temperature below room temperature. Moreover the drug delivery system is easy to prepare and still provides sufficient amounts and rates for release of the progestogenic compound for use in contraception and/or HRT.

FIG. 1:

In-vitro release rates of etonogestrel for a number of drug delivery systems described in examples 2-14 according to the invention and two comparative examples.

FIG. 2:

Curve fit of the vinyl acetate content of polyethylene vinylacetate copolymers summarized in Table II versus the saturation level of etonogestrel in these same copolymers at 25° C. and at 37° C.

DETAILED DESCRIPTION OF THE INVENTION

The advantages of the invention are obtained by designing the drug delivery system as described above. The drug delivery system comprises at least one compartment, which consists of two layers, i.e. a core and a skin. The skin is directly covering the core, giving the drug delivery system an uncomplicated design such that it can be prepared by an economically attractive preparation process.

In one embodiment the progestogenic compound is present in a concentration such that the core comprises the progestogenic compound being dissolved in the polyethylene vinylacetate copolymer up to a concentration below the saturation level at 25° C.

In another embodiment the concentration of the progestogenic compound below the saturation level at 25° C. in the core can be obtained by using polyethylene vinylacetate copolymer with a relatively high concentration of vinylacetate, that is, a copolymer containing in the range from 30 to 50 wt % vinylacetate copolymer. In a further embodiment the polyethylene vinylacetate copolymer in the core comprises in the range from 32 to 45 wt % vinylacetate. Use of such a polyethylene vinylacetate copolymer with a relatively high concentration of vinylacetate was found to result in decreased release of progestogenic compound from the core.

In one embodiment polyethylene vinylacetate copolymer has a wt % vinylacetate of 32 to 50% and in an even further embodiment has a wt % vinylacetate of 35 to 50%. The use of a polyethylene vinylacetate copolymer having such a high vinylacetate content for the core provides a system with an advantageous flexibility.

In another embodiment the skin is prepared from polyethylene vinylacetate copolymer comprising 1 to 15 wt % vinylacetate, and in an even further embodiment from polyethylene vinylacetate copolymer comprising 5 to 15 wt % vinylacetate.

In an even further embodiment a polyethylene vinylacetate content in the range of 1 to 15 wt % can advantageously be used in a drug delivery system having a skin with a thickness in the range from 10 to 110 µm. Such a skin thickness of less than about 110 µm is advantageous to obtain a good flexibility of the overall pharmaceutical delivery device. Furthermore the use of such skin thickness and vinylacetate content results in an advantageous low burst release.

In another embodiment polyethylene vinylacetate copolymer has a vinylacetate content of 14 to 28 wt % for the skin. Such vinylacetate content can advantageously be used in a pharmaceutical delivery device having a skin thickness in the range from 70 to 250 µm, for which it is especially easy to obtain a very good process consistency. A skin of polyethylene vinylacetate copolymer with a vinylacetate content of about 14 to 28 wt % is further advantageous, because it results in an advantageously low extent of aging of the material. Such aging can be chemical or physical. It is herein noticed that, without wishing to be bound to any kind of theory, aging can result in a gradual change in time of the release profile (properties) due to physical changes in the polymeric structure of the copolymer. The above embodiment thus results in an advantageously low extent of change of the release profile of the active ingredients after long-term storage.

The polyethylene vinylacetate copolymer can independently for core and skin be any commercially available polyethylene vinylacetate copolymer, such as for example the products available under the trade names: Elvax®, Evatane®, Lupolen V®, Movriton®, Ultrathene®, Ateva® and Vestypar® and further polyethylene vinylacetate copolymers marketed by for example Dupont (e.g. Dupont 760), Equistar (e.g. Equistar UE637-000), Huntsman (e.g. Huntsman PE1903) and Exxon Mobil (Fl00309). Suitable polyethylene vinylacetate copolymers for the core include the commercially available Ateva® 4030, Ateva® 3325, Evatane® 33-25 and Evatane® 40-55. Suitable polyethylene vinylacetate copolymers for the skin include the commercially available Ateva® 1070, Ateva® 1231 en Ateva® 1525 Evatane® 1020 VN3, Evatane® 1040 VN4 and Evatane® 1080 VN5.

The progestogenic compound of the subject invention can be any progestogen. In a further embodiment, the progestogenic compound is a steroidal progestogenic compound. Examples of suitable progestogenic compounds include compounds such as desogestrel, etonogestrel, levonorgestrel, norgestimate, gestodene, drospirenone or any other compound with progestogenic activity. In a particular embodiment the progestogenic compound is etonogestrel (3-keto desogestrel).

In a further embodiment, when the progestogenic compound is etonogestrel, such etonogestrel is present in the core in a concentration below the saturation level at 25° C. between 0.1 and 1.0 wt %, based on the weight of the core, and in an even further embodiment in a concentration between 0.3 and 0.8 wt %. In a particular embodiment such etonogestrel is present in the core in a concentration in the range of 0.4 to 0.7 wt %.

The estrogenic compound can be any estrogen. In a further embodiment, the estrogenic compound is a steroidal estrogenic compound. Examples of suitable estrogenic compounds include compounds such as estradiol, estriol, mestranol, estradiol-valerate and ethinyl estradiol. In a particular embodiment the estrogenic compound is ethinyl estradiol. In a further embodiment such ethinyl estradiol is present in the core in a concentration between 0.01 and 0.5 wt %, based on the weight of the core, and in an even further embodiment in a concentration between 0.05 and 0.2 wt %. In a particular embodiment such ethinyl estradiol is present in the core in a concentration in the range of 0.07 to 0.15 wt %.

In addition to the progestogenic compound and the estrogenic compound the drug delivery system can contain other drugs, e.g. anti-microbials. Such anti-microbials can be used for example to concomitantly treat and/or prevent sexually transmitted diseases (STD's) such as AIDS, chlamydia, herpes and gonorrhoea. The anti-microbial drug can be any antibacterial drug such as any antibiotic, any anti-viral agent, any anti-fungal agent or any anti-protozoal agent. An example of an anti-microbial drug contemplated to be incorporated into the vaginal ring of the subject invention is mandelic acid condensation polymer (Zanefeld et al. (2002), *Fertility and Sterility* 78(5): 1107-1115). Another example is dapivirine (4-[[4-[2,4,6-trimethylphenyl)amino-2-pyrimidinyl]amino] benzonitrile).

The improved drug delivery system according to the invention provides sufficient amounts and rates of release of the progestogenic compound for use in contraception and/or HRT. By these sufficient amounts and rates for release is understood that throughout the release period at each point in time a safe and sufficient effective amount of the progestogenic compound is released. In particular the release profile of the progestogenic compound may not be too steep. The mean release required is dependent on the use. In an even further embodiment for use in contraception the mean release may also not be too low. In one practical embodiment, when the progestogenic compound is etonogestrel, sufficient amounts and rates of release of etonogestrel for use in contraception are amounts and rates of release similar to those of Nuvaring®. In one embodiment the release of etonogestrel of such a drug delivery device on day 21 ($R_{21}$) is 80 μg/day or more. In a further embodiment the mean release of etonogestrel of such a drug delivery device lies in the range from 96 to 144 μg/day. In a further embodiment, the release of etonogestrel in such a drug delivery device is reflected by releases at $R_2$ and/or $R_{21}$, wherein $R_2$ lies in the range from 122-181 μg/day; and/or $R_{21}$ lies in the range from 82 to 121 μg/day. In an even further embodiment, the release of etonogestrel in such a drug delivery device is reflected by releases at $R_2$ and/or $R_{21}$, wherein $R_2$ lies in the range from 135-165 μg/day; and/or $R_{21}$ lies in the range from 85 to 115 μg/day. In a still even further embodiment, the release of etonogestrel in such a drug delivery device is reflected by releases at $R_2$ and/or $R_{21}$ wherein $R_2$ lies in the range from 140-160 μg/day; and/or $R_{21}$ lies in the range from 90 to 110 μg/day. In an even further embodiment, when the progestogenic compound is etonogestrel, $R_2$ is about 150 μg/day day and/or $R_{21}$ is about 100 μg/day.

In one embodiment the drug delivery system according to the invention is a cylindrical fibre, consisting of a cylindrical core and a skin covering this core. In a particular embodiment the cross sectional diameter of such a cylindrical fibre is between about 2.5 and 6 mm, in a specific embodiment between about 3.0 and 5.5 mm, and in another embodiment between about 3.5 and 4.5 mm and in yet another embodiment is 4.0 or 5.0 mm. In one embodiment, the surface of the core body is more than 800 mm$^2$, and in another embodiment more than 1000 mm$^2$ and in a further embodiment in the order of 1700-2200 mm$^2$ Significantly larger surfaces are possible, provided that the design (physical dimensions) of a drug delivery system intended for vaginal use prevents inconvenience for the subject.

The drug delivery system according to the invention can have several shapes, including but not limited to a spiral shape, a T-shape or a ring shape. In a specific embodiment the drug delivery system according to the invention is ring-shaped, i.e. is an annular drug delivery system. In one particular embodiment, the drug delivery system is a ring-shaped drug delivery system having an outer circumference of the ring of between 50 and 60 mm and in another embodiment between 52 and 56 mm.

The drug delivery system comprises at least one compartment having the characteristics as specified in the claims. In addition to this compartment one or more additional compartments can be present, making a total of for example two or three compartments. For example, an additional compartment can be added which is a placebo compartment or a compartment loaded with one or more other drugs. Such an extra compartment can be advantageous for example in practicing hormonal replacement therapy, where the ratio between progestogen and estrogen is different from the ratio suitable for contraception. Such an extra compartment can also be advantageous to administer, in addition to the progestogenic and estrogenic compounds, anti-microbial drugs to treat and/or prevent STD's such as AIDS, chlamydia, herpes and gonorrhoea, as suggested hereinabove.

In a specific embodiment, however, the drug delivery system consists of only one compartment, such compartment having the characteristics as specified in the claims.

In one specific embodiment the drug delivery system consisting of one or more compartments and comprising a progestogenic compound dissolved in a thermoplastic polyethylene vinylacetate copolymer whereby, if the delivery system consists of one compartment, the compartment comprises (i) a core of a thermoplastic polyethylene vinylacetate copolymer, said copolymer containing 30 to 50 wt % vinylacetate, and said core comprising a progestogenic compound, said progestogenic compound being dissolved in the polyethylene vinylacetate copolymer up to a concentration below the saturation level at 25° C., and an estrogenic compound; and (ii) a skin of a thermoplastic polyethylene vinylacetate copolymer covering the core, said copolymer containing 1 to 15 wt % vinylacetate, said skin being permeable for both compounds, and said skin having a thickness in the range of 10 to 110 μm;

if the delivery system consists of more than one compartment, only one compartment comprises (iii) the progestogenic compound, such progestogenic compound being dissolved in a core of a thermoplastic polyethylene vinylacetate copolymer up to a concentration below the saturation level at 25° C., said copolymer containing 30 to 50 wt % vinylacetate, and an estrogenic compound; and (iv) a skin of a thermoplastic polyethylene vinylacetate copolymer covering the core, said copolymer containing 1 to 15 wt % vinylacetate, said skin being permeable for both compounds, and said skin having a thickness in the range of 10 to 110 μm In a further embodiment the concentration of progestogenic compound in the core lies in the range of 0.3 to 0.8 wt %.

In an even further embodiment said skin has a thickness in the range of 20 to 100 μm. In a still further embodiment said skin has a thickness in the range of 30 to 70 μm. In a still even further embodiment the copolymer of the skin contains 1 to 14 wt % vinylacetate. In an even further embodiment the copolymer of the skin contains 1 to 12 wt % vinylacetate. Such drug delivery system has the further advantage that an advantageous low burst release can be obtained.

In another specific embodiment of the invention the drug delivery system consisting of one or more compartments and comprising a progestogenic compound dissolved in a thermoplastic polyethylene vinylacetate copolymer whereby, if the delivery system consists of one compartment, the compartment comprises (i) a core of a thermoplastic polyethylene vinylacetate copolymer, said copolymer containing 30 to 50 wt % vinylacetate, and said core comprising a progestogenic compound, such progestogenic compound being dissolved in the polyethylene vinylacetate copolymer up to a concentration below the saturation level at 25° C., and an estrogenic compound; and (ii) a skin of a thermoplastic polyethylene vinylacetate copolymer covering the core, said copolymer containing 14 to 28 wt % vinylacetate, said skin being permeable for both compounds, and said skin having a thickness of 70 to 250 μm;

if the delivery system consists of more than one compartment, only one compartment comprises (iii) the progestogenic compound, such progestogenic compound being dissolved in a core of a thermoplastic polyethylene vinylacetate copolymer up to a concentration below the saturation level at 25° C., said copolymer containing 30 to 50 wt % vinylacetate, and an estrogenic compound; and (iv) a skin of a thermoplastic polyethylene vinylacetate copolymer covering the core, said copolymer containing 14 to 28 wt % vinylacetate, said skin being permeable for both compounds, and said skin having a thickness of 70 to 250 µm.

In a further embodiment the concentration of progestogenic compound in the core lies in the range of 0.3 to 0.8 wt %. In a still further embodiment the thickness of said skin is in the range from 75 to 250 µm, and in an even further embodiment the thickness of said skin is in the range from 80 to 180 µm. In a still further embodiment the thickness of said skin is 100 to 250 µm. And in a further embodiment the thickness of said skin is 110 to 250 µm. In an even further embodiment the vinylacetate content of the thermoplastic skin lies in the range from 14 to 28 wt % vinylacetate. And in a still further embodiment the vinylacetate content of the skin is from 16 to 25 wt %.

Such drug delivery system shows an improved stability in that the release profile is less and in some cases not or nearly not influenced by the aging of the skin copolymer.

The drug delivery system of the subject invention can be manufactured by any known process of extrusion, such as co-extrusion and/or blend-extrusion. For example, the drug-loaded core and the non-medicated outer layer can be co-extruded. The fibres thus obtained can be cut into pieces of the required length and each piece can be assembled to, for example, a ring-shaped device in any suitable manner. In one embodiment the fibres are cut into pieces with a length in the range from 135 to 185 mm and in a further embodiment into pieces with a length in the range 155 to 159 mm, and in one further embodiment into pieces with a length of about 157 mm. Subsequently the pieces are assembled into a ring-shaped device. The assembly into a ring-shaped device can be carried out in any manner suitable for this purpose. For example the ends of the fibre can be joined together with an adhesive; or by placing the fibre in a mould at an elevated temperature (e.g. a temperature of above about 40° C.) and injecting molten high density polyethylene in between the fibre ends, whereafter the prepared ring is cooled; or by joining the fibre ends together by welding. In one embodiment a ring-shaped drug delivery system is prepared by welding the fibre ends together at a welding temperature of 130° C. and a welding time of 15 to 20 seconds, on a TWI mono-welding unit.

The present invention hence also provides a method of manufacturing a drug delivery system in the shape of a ring comprising the steps of:
(i) producing a medicated homogenous polyethylene vinylacetate copolymer core granulate, comprising a progestogenic and an estrogenic compound;
(ii) co-extruding the core granulate with a polyethylene vinylacetate copolymer skin granulate, resulting in a copolymer fibre comprising a core covered by a skin;
(iii) assembling the fibre into a ring.

As indicated above the loaded (medicated) homogenous polymer can be a suitable polyethylene vinylacetate copolymer loaded with a suitable progestogenic compound and a suitable estrogenic compound. The polymer for the skin can be another suitable polyethylene vinylacetate copolymer.

The thermoplastic polyethylene vinylacetate copolymer core granulate can be prepared by grounding the polyethylene vinylacetate copolymer for the core; dry powder mixing the grounded polymer for the core with the progestogenic and/or estrogenic compound to be loaded in the core; blend extruding the resulting powder mixture; and cutting the resulting loaded polymer strands into granules, thereby obtaining a core granulate. The core granulate can be lubricated with a lubricant. Suitable lubricants include for example irgawax, talc, aerosil and stearates such as magnesium stearate.

The prepared rings can for example be packed in a suitable sachet, such as described in e.g. EP-A-1037812, optionally after being sterilized or disinfected.

The drug delivery system according to the invention is especially suitable for use in the field of female contraception and hormone replacement therapy. The drug delivery system can advantageously be used for the simultaneous controlled release of a progestogenic compound and estrogenic compound. The drug delivery system may—as already indicated above—also be used to concomitantly provide contraception and combat microbial disease. The microbial infection to be treated and/or prevented can be any bacterial, viral, fungal or protozoal infection. Specifically, sexually transmitted diseases such as HIV, chlamydia, gonorrhoea, or herpes may be treated by incorporation of an anti-microbial agent into the ring of the subject invention.

The invention further provides a method of contraception which comprises the steps of a) positioning a drug delivery system of the subject invention within the female vaginal tract and b) retaining the system within the vaginal tract for at least approximately 21 days. In addition the invention provides a method of concomitantly providing contraception whilst simultaneously treating or preventing a sexually transmitted disease which comprises the steps of positioning a drug delivery system of the subject invention within the female vaginal tract and retaining the system within the vaginal tract for at least approximately 21 days.

In one embodiment, the drug delivery system is removed after about 21 days for an approximate one week period to permit menstruation. In other embodiments, the drug delivery system is removed after about 42, 63, 84, 105, 126, 147, 186, 189, 210, 231, 252, 273, 294, 315, 336 or 357 days or after each month for an approximate one week period to permit menstruation. After the approximate week to allow for menstruation, a new drug delivery system of the subject invention is inserted into the female vagina to provide contraception in the next female cyclus or cycli.

In another embodiment, the drug delivery system is removed after about 21 days and a subsequent drug delivery system is inserted directly after the previous drug delivery system has been removed, i.e. without an approximate one week period to permit menstruation. In other embodiments, the drug delivery system is removed after about 42, 63, 84, 105, 126, 147, 186, 189, 210, 231, 252, 273, 294, 315, 336 or 357 days or after each month.

In a further embodiment this invention provides the use of the drug delivery system described above for the manufacture of a contraceptive kit or kit for hormone-replacement therapy.

In a still further embodiment this invention provides the use of the drug delivery system described above for the manufacture of a combination preparation to provide contraception whilst simultaneously to treat and/or prevent a sexually transmitted disease.

The invention is further illustrated by the following non-limiting examples.

Preparation of the Examples

Examples of ring-shaped drug delivery systems, comprising the polyethylene vinylacetate copolymer materials for skin and core, the dimensions and the concentrations of active ingredients as indicated in Table I, were prepared as follows:

Etonogestrel (a progestogenic compound) and ethinyl estradiol (an estrogenic compound) were mixed homogeneously through the copolymer used for the core.

The mixing of the core material of examples 1-10 was performed by dry powder mixing the micronized compounds and copolymer powder in a stainless steel drum using a Rhöfrad (Barrel-hoop principle) with a fixed rotation speed of approximately 46 rpm for 15 minutes.

The mixing of the core material of examples 12-14 was performed by dry powder mixing the micronized compounds and copolymer powder in a stainless steel drum using a Rhöfrad (Barrel-hoop principle) with a fixed rotation speed of approximately 26 rpm for 60 minutes.

For preparing the core material of example 11, the micronized compounds were mixed with copolymeric granulate instead of powder. Mixing was carried out in a stainless steel drum using a Rhöfrad (Barrel-hoop principle) with a fixed rotation speed of approximately 26 rpm for 60 minutes.

Subsequently the homogenized mixture was blend extruded using a 25 mm co-rotating double screw blend extruder and the resulting medicated polymer strands were cut into granules using an Scheer granulator. According to this process a drug-loaded core granulate was manufactured.

After granulation the drug-loaded core granulate for examples 11-14 was sieved. The drug-loaded core granulate for all examples was lubricated with magnesium stearate in order to facilitate the next processing step (co-extrusion). In examples 1-10 the drug loaded core granulate was co-extruded with the copolymer used for the skin in a Plastic Machinenbau co-extruder. In examples 11-14 the drug loaded core granulate was co-extruded with the copolymer used for the skin in a Fourne 35-22 co-extruder. The skin and core materials were combined in a self-centering spinning block from which two co-extruded fibres were produced. For each fibre, 2 separate spinning pumps (to control the volume flow rate (melt flow) of each layer) were applied. The capillaries applied had a diameter of 3.6 mm and all fibres were extruded at an extrusion temperature of 110° C.

The drug loaded fibers of examples 1-10 were processed at an extrusion speed of 1 m/min; the drug loaded fibres of examples 12-14 were processed at an extrusion speed of 6.7 m/min; and the drug loaded fiber of example 11 was processed at an extrusion speed of 2.0 m/min Upon leaving the spinnerette, the skin-core fibre was led through air and subsequently through a water bath (10-20° C.) by means of a take-off unit. The outer diameter of the fibre was measured on-line continuously using a laser micrometer. Hereafter the fibres were cut into pieces of about 157 mm. For examples 1-10 the ends of the fibre pieces were subsequently glued together with Loctite® acrylate glue. The ends of the fibre pieces for examples 11-14 were welded together at 130° C. for 17 seconds to form a ring. The characteristics of the materials that were used for skin and core of each example have been taken up in Table II.

Determination of Saturation Level

To determine the saturation level of etonogestrel of the polyethylene vinylacetate copolymers used, films of about 200 mm were prepared by film extrusion. The films were cut in pieces of 5×5 cm and subsequently immersed in saturated aqueous solutions of etonogestrel at 25° C. After 6 weeks of incubation, equilibrium was reached and the films were analyzed for the content of etonogestrel. The pieces were extracted with methanol for 20 hours at a temperature of 70° C. and subsequently the concentration of etonogestrel was assessed by HPLC, using a Novapak C18 column of 3.9×150 mm at column temperature of 30° C., a mobile phase of methanol/water/THF (46/48/6 v/v %), a flow rate of 1.5 ml/min, and an injection volume of 40 µA Detection was carried out by UV detection at 210 nm.

Fibre Dimension

The fibre dimensions (outer diameter and skin thickness) were determined directly after processing. The outer diameter was determined by means of laser thickness gauge (Mitutoyo). The skin thickness was determined using a microscope (Jena).

Vinylacetate Content of the Copolymer

The vinylacetate content for the copolymers used in the examples 2-14 as specified in II, IV, V and VI was determined by 1H NMR in a DRX600\NMR spectrometer (Bruker Spectrospin, Switzerland). For the NMR method 15-20 mg of slices of about 3-5 mg originating from different parts of the sample were mixed with 0.7 ml of tetrachloroethane-$d_2$. Subsequently the NMR tube was heated in an oil bath during 15-18 hours at 100° C. Hereafter a proton spectrum was acquired at 90-100° C. with 128 scans and a D1 of 5 seconds to assure complete relaxation. The spectrum was processed by applying an exponential multiplication of 0.3 Hz followed by Fourier transformation. The spectrum was integrated and the integral of the C$\underline{H}$O(C=O)CH3 group was set at 1. The vinylacetate content was calculated with formula I:

$$vinylacetate(\%) = \frac{y * M_{VA}}{[(x-2*y)/4] * M_{CH2-CH2} + y * M_{VA}} * 100 \quad (I)$$

wherein:
x=integral CH2
y=integral C$\underline{H}$O(C=O)CH3
$M_{VA}$=molecular weight VA (86)
$M_{CH2-CH2}$=molecular weight MCH2-CH2 (28)

With y set at 1(see above) the formula is reduced to formula II:

$$vinylacetate(\%) = \frac{86}{(x-2)*7+86} * 100 \quad (II)$$

The measurement was performed in duplicate using two different samples. The vinylacetate content was calculated from the obtained spectrum.

In-Vitro Release Rate

The in-vitro release rate of etonogestrel for examples 1-14 was determined by immersing the samples in 200 ml water of 37° C. under continuous stirring at 750 rpm. In order to maintain sink conditions the water in the containers was refreshed daily by an auto-sampler. The etonogestrel concentration was determined daily by HPLC, using a Novapak C18 column of 3.9×150 mm at column temperature of 30° C., a mobile phase of acetonitril:water (30/70 v/v %), a flow rate of 1.5 ml/min, and an injection volume of 10 l. Detection was carried out by UV detection at 205 nm. (see also the article of J. A. H. van Laarhoven et al., International Journal of Pharmaceutics 232 (2002) pages 163-173).

Stability

The dimensions and the concentrations of active ingredients of the examples are summarized in Table I and the characteristics of the material used is summarized in Table II. An overview of the release profiles of etonogestrel for examples 1-14 and for the commercially available Nuvaring®, which is a product according to EP-A-0876815, are depicted in FIG. 1.

Because of the concentration above the saturation level at 25° C., etonogestrel in the samples of Nuvaring® and comparative example 1 may eventually crystallize out onto the skin of the device, which is undesirable.

As illustrated by Table III and FIG. 1, examples 2-14 show that with drug delivery systems according to the invention, which have a concentration below saturation level at 25° C., a similar and sufficient release profile of etonogestrel for use in contraception and/or HRT is still obtained.

TABLE I

Description of the materials, concentrations and variables used in examples 1-14.

| Example | Core material | Skin material | Fibre diameter (cm) | Skin thickness (cm) | Etono-gestrel (wt %) | Ethinyl estradiol (wt %) |
|---|---|---|---|---|---|---|
| Nuvaring® Comparative | Evatane® 28-25 | Evatane® 1020 | 0.4 | 0.011 | 0.69 | 0.16 |
| Comparative 1 | Evatane® 33-25 | Evatane® 1020 | 0.4 | 0.0083 | 0.69 | 0.13 |
| 2 | Evatane® 33-25 | Evatane® 1020 | 0.4 | 0.0042 | 0.4 | 0.075 |
| 3 | Evatane® 33-25 | Evatane® 1020 | 0.5 | 0.0061 | 0.4 | 0.075 |
| 4 | Evatane® 33-25 | Evatane® 1040 | 0.4 | 0.0091 | 0.4 | 0.075 |
| 5 | Evatane® 33-25 | Evatane® 1080 | 0.4 | 0.0134 | 0.4 | 0.075 |
| 6 | Evatane® 40-55 | Evatane® 1020 | 0.4 | 0.0059 | 0.69 | 0.13 |
| 7 | Evatane® 40-55 | Evatane® 1020 | 0.4 | 0.0047 | 0.6 | 0.11 |
| 8 | Evatane® 40-55 | Evatane® 1020 | 0.5 | 0.0057 | 0.6 | 0.11 |
| 9 | Evatane® 40-55 | Evatane® 1040 | 0.4 | 0.0099 | 0.6 | 0.11 |
| 10 | Evatane® 40-55 | Evatane® 1080 | 0.4 | 0.0152 | 0.6 | 0.11 |
| 11 | Ateva® 4030 | Ateva® 1525 | 0.4 | 0.0084 | 0.6 | 0.10 |
| 12 | Ateva® 3325 | Ateva® 1070 | 0.4 | 0.0036 | 0.4 | 0.075 |
| 13 | Ateva® 3325 | Ateva® 1231 | 0.4 | 0.0065 | 0.4 | 0.075 |
| 14 | Ateva® 3325 | Ateva® 1525 | 0.4 | 0.0099 | 0.4 | 0.075 |

TABLE II

Description of the characteristics of the materials used in examples 1-14.

| Material | Vinyl-acetate[1] (wt %) | Saturation level of etonogestrel at 25° C. (wt %) | Saturation level of etonogestrel at 37° C. (wt %) |
|---|---|---|---|
| Evatane® 28-25 | ±28 | 0.35 | 0.44 |
| Evatane® 33-25 | ±33 | 0.50 | 0.67 |
| Evatane® 40-55 | ±40 | 0.75 | 1.12 |
| Evatane® 1020 | ±9 | 0.046 | 0.055 |
| Evatane® 1040 | ±14 | 0.10 | 0.161 |
| Evatane® 1080 | ±18 | 0.16* | 0.21* |
| Ateva® 1070 | ±9 | 0.045* | 0.066* |
| Ateva® 1231 | ±12 | 0.078* | 0.107* |
| Ateva® 1525 | ±15 | 0.12* | 0.155* |
| Ateva® 4030 | ±40 | 0.75* | 1.126* |
| Ateva® 3325 | ±33 | 0.50* | 0.701* |

Figure 2:
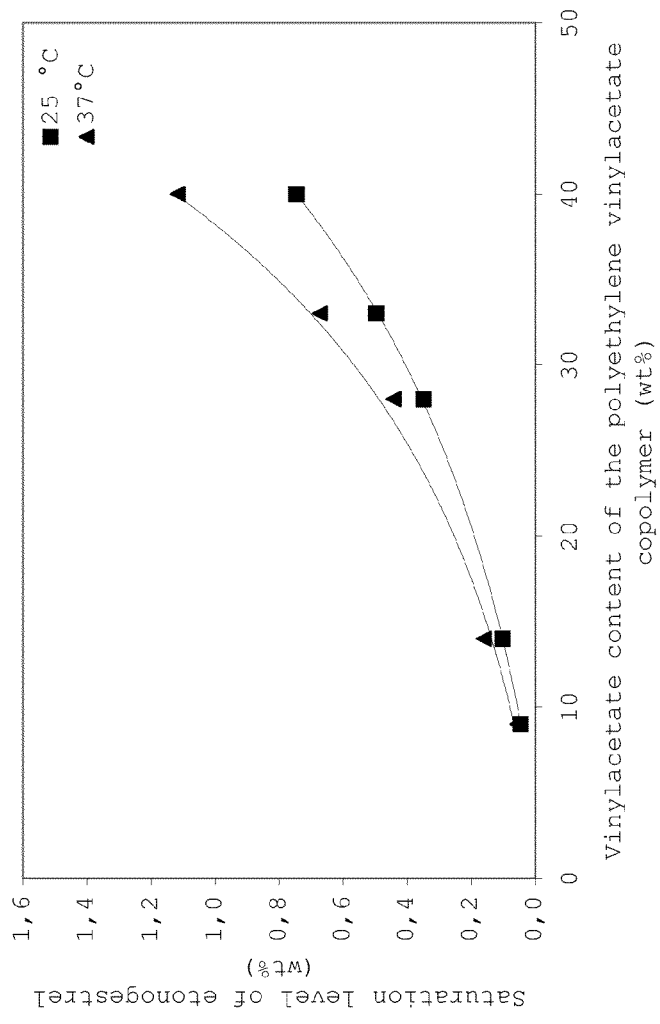

[1] Vinylacetate content taken from product specification of the supplier
*these saturation levels were obtained by interpolation from curve fit of the vinylacetate content of the material versus saturation level as shown in FIG. 2.

TABLE III

Release rates for examples 1-14

| Example | Concentration above/below saturation level | Vinylacetate content of the core (wt %) | Vinylacetate content of the skin (wt %) | R2 g/day | R21 g/day |
|---|---|---|---|---|---|
| Nuvaring Comparative | Above | 28[1] | 9[1] | 151.0 | 99.3 |
| Comparative 1 | Above | 34 | 10 | 154.5 | 102.6 |
| 2 | Below | 34 | 10 | 140.7 | 81.3 |
| 3 | Below | 34 | 10 | 124.0 | 82.8 |
| 4 | Below | 34 | 15 | 165.2 | 86.9 |
| 5 | Below | 34 | 20 | 207.3 | 91.9 |
| 6 | Below | 40 | 10 | 102.9 | 70.6 |
| 7 | Below | 40 | 10 | 119.9 | 80.1 |
| 8 | Below | 40 | 10 | 117.9 | 86.1 |
| 9 | Below | 40 | 15 | 146.4 | 90.8 |
| 10 | Below | 40 | 20 | 184.4 | 101.1 |
| 11 | Below | 42 | 15 | 188.1 | 113 |
| 12 | Below | 32 | 9 | 175.3 | 90 |
| 13 | Below | 32 | 11 | 147.0 | 82 |
| 14 | Below | 32 | 15 | 187.5 | 92 |

R2 and R21 represent the release rates on day 2 and day 21 respectively.
[1] Vinylacetate content for this sample was based on product specification of the supplier Burst Release The extent of burst release is indicated by the burst release factor. The burst release factor was determined at t=0 with formula III:

$$\left(\frac{R_1 - R_2}{R_2}\right) * 100 \tag{III}$$

wherein:
$R_1$ is release of the sample on day 1
$R_2$ is release of the sample on day 2.
The burst release factor of examples 1-14 was determined at t=0.
The results are shown in Table IV.

TABLE IV

Results on the burst release at t = 0 of examples 1-14

| Example | Etono-gestrel (wt %) | Vinylacetate content of the core (wt %) | Vinylacetate content of the skin (wt %) | Skin thickness (cm) | Burst release factor at t = 0[1] (%) |
|---|---|---|---|---|---|
| Nuvaring | 0.69 | 28[2] | 9[2] | 0.011 | 33.5 |
| Comparative |  |  |  |  |  |
| Comparative 1 | 0.69 | 34 | 10 | 0.0083 | 18.6 |
| 2 | 0.4 | 34 | 10 | 0.0042 | 13.9 |
| 3 | 0.4 | 34 | 10 | 0.0061 | 15.0 |
| 4 | 0.4 | 34 | 15 | 0.0091 | 21.7 |
| 5 | 0.4 | 34 | 20 | 0.0134 | 26.3 |
| 6 | 0.69 | 40 | 10 | 0.0059 | 12.8 |
| 7 | 0.6 | 40 | 10 | 0.0047 | 11.7 |
| 8 | 0.6 | 40 | 10 | 0.0057 | 12.7 |
| 9 | 0.6 | 40 | 15 | 0.0099 | 19.4 |
| 10 | 0.6 | 40 | 20 | 0.0152 | 24.0 |
| 11 | 0.6 | 42 | 15 | 0.0084 | 16.1 |
| 12 | 0.4 | 32 | 9 | 0.0036 | 16.1 |
| 13 | 0.4 | 32 | 11 | 0.0065 | 17.1 |
| 14 | 0.4 | 32 | 15 | 0.0099 | 22.9 |

[1] The burst release factor of Nuvaring, samples 1-10 and samples 11-14 was based on the mean burst release factor of respectively 4, 3 and 6 samples.
[2] Vinylacetate content for this sample was based on product specification of the supplier.

To exclude influence of the material of the core, only examples with a similar etonogestrel and vinylacetate content in the core were compared. As illustrated in table IV, a drug delivery system with a relatively thin polyethylene vinylacetate copolymer skin having a relatively low vinylacetate content results in an advantageously low burst release.

Flexibility

Furthermore the flexibility of examples 1-14 was determined and compared with the flexibility of Nuvaring®. The flexibility was determined by means of a press-pull apparatus (LR 5K, Lloyd Instruments). The entire ring-shaped drug delivery system in a relaxed state was fixed in two V-shaped holders. The distance between the corners of the V-shaped profiles is 54 mm. Subsequently the holders were pressed towards each other with a predetermined speed of 50 mm/min until the distance between the corners of the V-shaped profiles was 21 mm. The force in Newton that was applied to the ring-shaped drug delivery system to bring about a certain deformation of the ring was measured at predetermined spots. That is, it was measured when the deformation comprised 10 mm (i.e. at a distance of 44 mm), 20 mm (i.e. at a distance of 34 mm), 30 mm (i.e. at a distance of 24 mm) and 33 mm (i.e. at a distance of 21 mm). The results are summarized in Table V.

TABLE V

Flexibility results for examples 1-14

| Example | Vinylacetate content of the core (wt %) | Vinylacetate content of the skin (wt %) | Fibre diameter (cm) | Skin thickness (cm) | Force at 10 mm(N) | Force at 20 mm(N) | Force at 30 mm(N) | Force at 33 mm(N) |
|---|---|---|---|---|---|---|---|---|
| Nuvaring | 28[2] | 9[2] | 0.4 | 0.011 | 1.10 | 2.00 | 4.00 | 5.10 |
| 1 | 34 | 10 | 0.4 | 0.0083 | 0.78 | 1.37 | 2.90 | 3.82 |
| 2 | 34 | 10 | 0.4 | 0.0042 | 0.61 | 1.13 | 2.43 | 3.25 |
| 3* | 34 | 10 | 0.5 | 0.0061 | 1.34 | 2.56 | 5.79 | 7.56 |
| 4 | 34 | 15 | 0.4 | 0.009 | 0.71 | 1.28 | 2.71 | 3.60 |
| 5 | 34 | 20 | 0.4 | 0.0134 | 0.72 | 1.30 | 2.82 | 3.73 |
| 6 | 40 | 10 | 0.4 | 0.0059 | 0.43 | 0.73 | 1.42 | 1.84 |
| 7 | 40 | 10 | 0.4 | 0.0047 | 0.40 | 0.69 | 1.35 | 1.75 |
| 8* | 40 | 10 | 0.5 | 0.0057 | 0.77 | 1.37 | 2.81 | 3.76 |
| 9 | 40 | 15 | 0.4 | 0.0099 | 0.54 | 0.96 | 1.78 | 2.20 |
| 10 | 40 | 20 | 0.4 | 0.0152 | 0.56 | 1.05 | 2.14 | 2.78 |
| 11 | 42 | 15 | 0.4 | 0.0084 | 0.32 | 0.55 | 1.07 | 1.37 |
| 12 | 32 | 9 | 0.4 | 0.0036 | 0.54 | 1.02 | 2.34 | 3.17 |
| 13 | 32 | 11 | 0.4 | 0.0065 | 0.69 | 1.27 | 2.82 | 3.74 |
| 14 | 32 | 15 | 0.4 | 0.0099 | 0.67 | 1.24 | 2.78 | 3.73 |

*Examples 3 and 8 show a relatively low flexibility due to the fact that the cross-sectional diameter of these fibres is 0.5 cm.

For the fibres having the same cross-sectional diameter of 0.4 cm it can be concluded that the ring-shaped drug delivery systems comprising a core with a higher vinylacetate content show a much higher flexibility when compared to Nuvaring ®.

[2] Vinylacetate content for this sample was based on product specification of the supplier Ring Shaped Drug Delivery Systems Comprising a Skin Prepared from Polypolyethylene Vinylacetate Copolymer with a High Vinylacetate Content.

During storage, the polyethylene vinylacetate copolymer ages. During this aging process crystalline and amorph domains in the polyethylene vinylacetate copolymer rearrange. As a result of the aging of the copolymer, the release of active ingredients, here etonogestrel, can change. The extent of aging of the copolymer is indicated by the Aging factor. The Aging factor was determined with formula IV:

$$\text{Aging} = \left(1 - \frac{R_{2,\text{after\_storage}}}{R_{2,t=0}}\right) * 100\% \quad (IV)$$

wherein
$R_{2,t=0}$=Release on day 2 at t=0
$R_{2,\text{after\_storage}}$=Release on day 2 after the indicated storage time The aging behaviour for examples 1-10 and 11-14 has been tested under real-time conditions (i.e. storage for 8 months at 20° C. respectively 3 months at 25° C.) and under accelerated conditions (i.e. storage for 5 months respectively 3 months at 40° C.). After storage the release of etonogestrel on day 2 was determined and the aging factor calculated. The results are given in Table VI.

TABLE VI

Aging for examples 1-10 after 5 months storage at 40° C.

| Example | Etonogestrel (wt %) | Vinylacetate content of the core (wt %) | Vinylacetate content of the skin (wt %) | Skin thickness (cm) | $R_{2, t=0}$ g/day/ sample) | $R_{2, t=5\, mnd}$ g/day/ sample) | Aging factor (%) |
|---|---|---|---|---|---|---|---|
| 1 | 0.69 | 34 | 10 | 0.0083 | 154.5 | 140.9 | 8.8 |
| 2 | 0.4 | 34 | 10 | 0.0042 | 140.7 | 130.4 | 7.3 |
| 3 | 0.4 | 34 | 10 | 0.0061 | 124.0 | 117.4 | 5.3 |
| 4 | 0.4 | 34 | 15 | 0.0091 | 165.2 | 159.2 | 3.7 |
| 5 | 0.4 | 34 | 20 | 0.0134 | 207.3 | 207.6 | 0 |
| 6 | 0.69 | 40 | 10 | 0.0059 | 102.9 | 91.3 | 11.3 |
| 7 | 0.6 | 40 | 10 | 0.0047 | 119.9 | 108.8 | 9.2 |
| 8 | 0.6 | 40 | 10 | 0.0057 | 117.9 | 105.6 | 10.5 |
| 9 | 0.6 | 40 | 15 | 0.0099 | 146.4 | 136.3 | 6.9 |
| 10 | 0.6 | 40 | 20 | 0.0152 | 184.4 | 183.3 | 0.6 |

To exclude influence of the material of the core, only examples with a similar etonogestrel and vinylacetate content in the core are to be compared. The results in Table VI illustrate that after 5 months storage at 40° C., drug delivery systems with a relatively thick polyethylene vinylacetate copolymer skin having a relatively high vinylacetate content show less aging.

The invention claimed is:

1. A drug delivery system consisting of one or more compartments, said compartments comprise progestogenic compound dissolved in a thermoplastic polyethylene vinylacetate copolymer whereby,
   if the delivery system consists of one compartment, the compartment comprises
   (i) a core of a thermoplastic polyethylene vinylacetate copolymer containing 32 to 45 wt % vinylacetate comprising the progestogenic compound, the progestogenic compound being dissolved in the polyethylene vinylacetate copolymer at a concentration below the saturation level at 25° C. between 0.1 and 1.0 wt %, based on the weight of the core, and an estrogenic compound; and
   (ii) a skin of a thermoplastic polyethylene vinylacetate copolymer covering the core, the copolymer containing 1 to 15 wt % vinylacetate, the skin being permeable for both compounds, and the skin having a thickness in the range of 10 to 110 µm;
   if the delivery system consists of more than one compartment, only one compartment comprises
   (iii) the progestogenic compound, the progestogenic compound being dissolved in a core of a thermoplastic polyethylene vinylacetate copolymer containing 32 to 45 wt % vinylacetate at a concentration below the saturation level at 25° C. between 0.1 and 1.0 wt %, based on the weight of the core, and an estrogenic compound; and
   (iv) a skin of a thermoplastic polyethylene vinylacetate copolymer covering the core, the copolymer containing 1 to 15 wt % vinylacetate, the skin being permeable for both compounds, and the skin having a thickness in the range of 10 to 110 µm,
   wherein the drug delivery system is physically stable when stored at or above room temperature.

2. A drug delivery system according to claim 1, wherein the progestogenic compound is a steroidal progestogenic compound and the estrogenic compound is a steroidal estrogenic compound.

3. A drug delivery system according to claim 1, wherein the progestogenic compound is etonogestrel.

4. A drug delivery system according to claim 3, wherein the release on day 21 of etonogestrel of the drug delivery system is 80 µg/day or more.

5. A drug delivery system according to claim 1, wherein the estrogenic compound is ethinyl estradiol.

6. A drug delivery system according to claim 1, wherein the system is ring-shaped.

7. A drug delivery system according to claim 1, wherein the drug delivery system consists of one compartment.

8. A drug delivery system according to claim 1, wherein the drug delivery system is a drug delivery system for intravaginal use.

9. A drug delivery system according to claim 1, wherein the skin has a thickness in the range of 20 to 100 µm.

10. A drug delivery system according to claim 1, wherein the skin has a thickness in the range of 30 to 70 µm.

11. A drug delivery system according to claim 1, wherein the polyethylene vinylacetate copolymer of the skin is a copolymer containing 1 to 14 wt % vinylacetate.

12. A drug delivery system according to claim 1, wherein the polyethylene vinylacetate copolymer of the skin is a copolymer containing 1 to 12 wt % vinylacetate.

13. A drug delivery system according to claim 1, wherein the skin has a thickness in the range of 110 to 250 μm.

14. A drug delivery system according to claim 1, wherein the polyethylene vinylacetate copolymer of the skin is a copolymer containing 16 to 25 wt % vinylacetate.

15. A contraceptive kit or kit for hormone-replacement therapy comprising the drug delivery system according to claim 1.

16. A combination preparation to provide contraception while simultaneously to treat a sexually transmitted disease comprising the drug delivery system according to claim 1.

* * * * *